(12) United States Patent
Ross (10) Patent No.: US 8,990,040 B2
(45) Date of Patent: Mar. 24, 2015

(54) SYSTEM AND METHOD FOR CORRECTING FAULT CONDITIONS IN SOFT-FIELD TOMOGRAPHY

(75) Inventor: Alexander Seth Ross, Albany, NY (US)

(73) Assignee: General Electric Company, Niskayuna, NY (US)

( * ) Notice: Subject to any disclaimer, the term of this patent is extended or adjusted under 35 U.S.C. 154(b) by 646 days.

(21) Appl. No.: 12/976,656

(22) Filed: Dec. 22, 2010

(65) Prior Publication Data

US 2012/0166127 A1 Jun. 28, 2012

(51) Int. Cl.
| | |
|---|---|
| G01C 19/00 | (2013.01) |
| G01C 25/00 | (2006.01) |
| G01D 18/00 | (2006.01) |
| G01F 25/00 | (2006.01) |
| A61B 5/05 | (2006.01) |
| A61B 5/053 | (2006.01) |
| A61B 5/00 | (2006.01) |

(52) U.S. Cl.
CPC ............ *A61B 5/0536* (2013.01); *A61B 5/6843* (2013.01); *A61B 5/7221* (2013.01)
USPC ......................................... 702/104; 600/547

(58) Field of Classification Search
USPC ................... 702/104, 40, 183, 185; 600/301, 600/437–472, 425, 547
See application file for complete search history.

(56) References Cited

U.S. PATENT DOCUMENTS

| | | | |
|---|---|---|---|
| 5,544,662 | A | 8/1996 | Saulnier et al. |
| 7,142,919 | B2 | 11/2006 | Hine et al. |
| 7,627,362 | B2 | 12/2009 | Gregory et al. |
| 2003/0216630 | A1 * | 11/2003 | Jersey-Willuhn et al. ..... 600/407 |
| 2005/0251062 | A1 * | 11/2005 | Choi et al. ..................... 600/547 |
| 2008/0221834 | A1 | 9/2008 | Damodharan et al. |
| 2011/0148443 | A1 * | 6/2011 | Maktura ....................... 324/705 |
| 2012/0245436 | A1 * | 9/2012 | Rutkove et al. ............... 600/301 |

OTHER PUBLICATIONS

European Search Report and Written Opinion, dated Oct. 30, 2012, pp. 1-6.
Response to European Written Opinion, dated May 28, 2013, pp. 1-14.

* cited by examiner

*Primary Examiner* — John Breene
*Assistant Examiner* — Manuel Rivera Vargas
(74) *Attorney, Agent, or Firm* — Scott J. Asmus (57) ABSTRACT

A soft-field tomography system includes a plurality of transducers configured for positioning at a surface of an object. An excitation driver is configured to generate a precomputed default excitation pattern for the plurality of transducers. A processor stores the precomputed default excitation pattern and a corresponding predicted response for the precomputed excitation pattern. The processor further stores one or more precomputed fault excitation patterns and corresponding predicted response for the fault excitation patterns corresponding to one or more fault conditions of the plurality of transducers. A response measurement device is configured to measure a response at one or more of the transducers to determine if a fault condition exists. If a fault condition exists, the processor at least one of instructs the excitation driver to generate a precomputed fault excitation pattern or uses a predicted response that corresponds to the fault condition for a soft field tomography process.

25 Claims, 8 Drawing Sheets

| | DEFAULT OR FAULT CONDITION | PRECALCULATED DEFAULT OR FAULT CONDITION EXCITATION PATTERN | PRECALCULATED DEFAULT OR FAULT CONDITION PREDICTED RESPONSE |
|---|---|---|---|
| 83 | 0 | W | $W^1$ |
| 84 | -1 | X | $X^1$ |
| | ⋮ | ⋮ | ⋮ |
| 86 | -1,2 | Y | $Y^1$ |
| | ⋮ | ⋮ | ⋮ |
| 88 | -1,3 | Z | $Z^1$ |
| | ⋮ | ⋮ | ⋮ |
| 89 | -1,4 | V | $V^1$ |
| | ⋮ | ⋮ | ⋮ |
| 90 | -1,5 | V | $V^1$ |
| | ⋮ | ⋮ | ⋮ |

SYSTEM AND METHOD FOR CORRECTING FAULT CONDITIONS IN SOFT-FIELD TOMOGRAPHY

BACKGROUND

The subject matter disclosed herein relates generally to data reconstruction systems and methods, and more particularly to systems and methods for correcting a fault condition in soft-field tomography.

Soft-field tomography, such as Electrical Impedance Spectroscopy (EIS) (also referred to as Electrical Impedance Tomography (EIT)), diffuse optical tomography, and related modalities may be used to measure the internal properties of an object, such as the electrical properties of materials of internal structures of an object (e.g., a region of a human body). For example, in EIS/EIT systems, object properties are determined by measuring the distribution of electrical properties of the interior of the object. Such EIS/EIT systems estimate the conductivity and/or permittivity of the materials within the volume based on current and voltage data acquired at the surface of the volume. Visual distributions of the estimates may then be reconstructed.

In soft-field tomography methods, excitations which may be optimized and/or controlled are applied for the generation of high-quality datasets having high signal to noise ratios. The excitations are typically precomputed, are applied to a configuration of transducers coupled to a surface of an object, and are highly dependent on a configuration of the transducers. However, during operation, one or more transducers may become inoperable. For example, one or more of the transducers may experience high contact impedance and/or become disconnected. Accordingly, the excitation patterns are no longer suitable for the transducer configuration. This can have a negative impact on system robustness and result in loss of data prior to user intervention to restore the nonfunctioning or underperforming transducer.

SUMMARY

In accordance with an embodiment, a soft-field tomography system is provided. The system includes a plurality of transducers configured for positioning at a surface of an object. The plurality of transducers correspond to a plurality of channels. An excitation driver is coupled to the plurality of channels and configured to generate a precomputed default excitation pattern for the plurality of transducers. A processor is electrically coupled to the excitation driver. The processor stores the precomputed default excitation pattern and a corresponding predicted response for the precomputed excitation pattern. The processor further stores precomputed fault excitation patterns and corresponding predicted responses for the fault excitation patterns corresponding to one or more fault conditions of the plurality of transducers. A response measurement device is configured to measure a response at one or more of the transducers to determine if a fault condition exists. If a fault condition exists, the processor at least one of instructs the excitation driver to generate a precomputed fault excitation pattern or uses a predicted response that corresponds to the fault condition for a soft field tomography process.

In accordance with another embodiment, a method for correcting a fault condition in a soft-field tomography system is provided. The method includes precomputing a default excitation pattern and a corresponding predicted response for a plurality of transducers arranged at a surface of an object. Fault excitation patterns and corresponding predicted responses for the fault excitation patterns that correspond to fault conditions in the plurality of transducers are precomputed. The default excitation pattern is applied to the object. A response is measured at one or more of the plurality of transducers to determine if a fault condition exists. If a fault condition exists, at least one of a fault excitation pattern is selected or a corresponding predicted response is used that corresponds to the fault condition.

In accordance with another embodiment, a processor for correcting a fault condition in a soft-field tomography system having a transducer fault module is provided. The transducer fault module is configured to precompute a default excitation pattern and a corresponding predicted response for a plurality of transducers arranged at a surface of an object. Fault excitation patterns and corresponding predicted responses for the fault excitation patterns corresponding to fault conditions in the plurality of transducers are precomputed. The default excitation pattern is applied to the object. A response is measured at one or more of the plurality of transducers to determine if a fault condition exists. If a fault condition exists, at least one of a fault excitation pattern is selected or a corresponding predicted response is used that corresponds to the fault condition.

BRIEF DESCRIPTION OF THE DRAWINGS

The presently disclosed subject matter will be better understood from reading the following description of non-limiting embodiments, with reference to the attached drawings, wherein below.

DETAILED DESCRIPTION

The foregoing summary, as well as the following detailed description of certain embodiments, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers, circuits or memories) may be implemented in a single piece of hardware or multiple pieces of hardware. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Various embodiments provide a system and method for soft-field tomography using, for example, an electrical impedance spectroscopy (EIS) system, also referred to as electrical impedance tomography (EIT) system. In general, an EIS system is provided that precalculates or precomputes default excitation patterns and corresponding predicted responses to the excitation patterns for a given transducer configuration. The EIS system also stores precalculated fault excitation patterns and corresponding predicted responses to the fault excitation patterns for a plurality of fault conditions that may occur during operation of the EIS system. For example, a fault condition may include high contact impedance at one or more transducers and/or a disconnection of one or more transducers. The EIS system in various embodiments detects fault conditions in real time during operation of the system. If a fault condition exists, the EIS system selects a fault excitation pattern and corresponding predicted response that corresponds to the fault condition and continues performing soft-field tomography measurements using the fault excitation pattern and corresponding predicted response. If the fault condition changes or corrects itself, the EIS system may select a new fault excitation pattern and corresponding predicted response and/or revert back to the default excitation pattern and corresponding predicted response.

Figure 1:
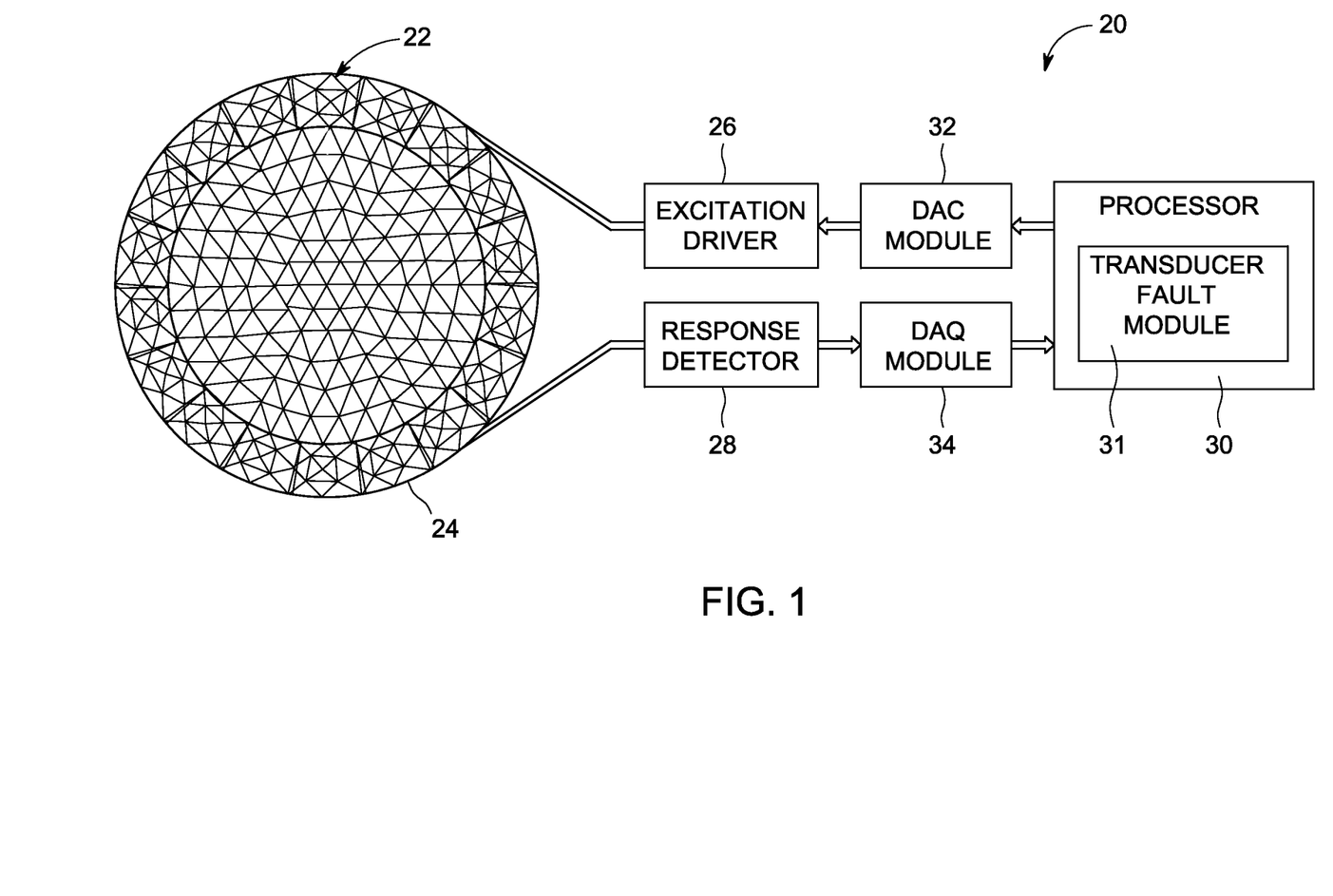
FIG. 1 is a simplified schematic block diagram illustrating a soft-field tomography system formed in accordance with various embodiments.
Figure 2:
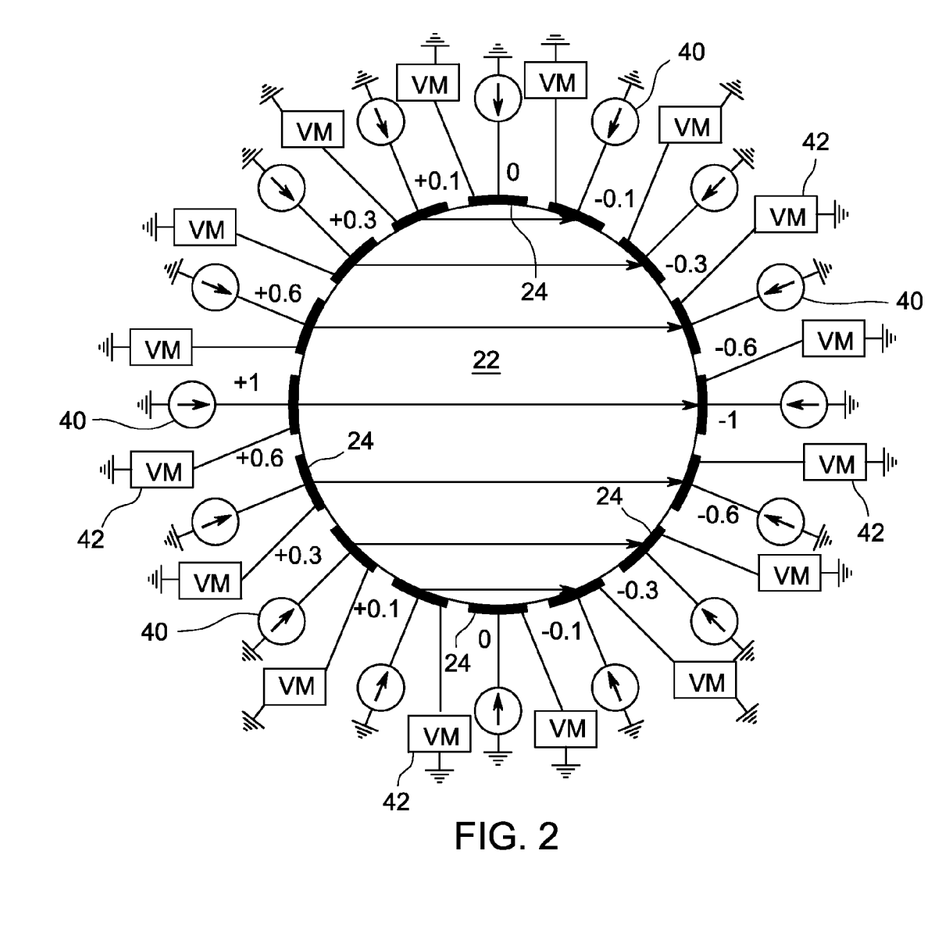
FIG. 2 is a simplified diagram illustrating an excitation configuration in accordance with various embodiments.

One embodiment of a soft-field tomography system 20 is illustrated in FIG. 1. For example, the soft-field tomography system 20 may be an Electrical Impedance Spectroscopy (EIS) system, also referred to as Electrical Impedance Tomography (EIT) system used to determine the electrical properties of materials within an object 22 as illustrated in FIG. 2. For example, the spatial distribution of electrical conductivity ($\sigma$) and/or permittivity ($\epsilon$) may be determined inside the object 22 or other volume. Thus, internal properties of the object 22 (e.g., a patient) may be determined. In the illustrated embodiment, the system 20 includes a plurality of transducers, which is this embodiment are transducers 24, positioned on a periphery of the object 22. In a healthcare application (e.g., patient monitoring or tissue characterization), the plurality of transducers 24 may be attached to the skin of a patient or subject. For example, the transducers 24 may be positioned at a surface of the object 22 (e.g. electrodes, thermal sources, ultrasound transducers), near the surface of the object 22 (e.g., radiofrequency antenna), or penetrating the surface of the object 22 (e.g., needle electrodes). Thus, the transducers 24 may take different forms, such as surface-contacting electrodes, standoff electrodes, capacitively coupled electrodes, conducting coils, and antennas, among others.

It should be noted that the soft-field tomography system 20 may be other types of systems. For example, the soft-field tomography system 20 may be a Diffuse Optical Tomography (DOT) system, a Near InfraRed Spectroscopy (NIRS) system, a thermography system, an elastography system or a microwave tomography system, among others. It also should be noted that as used herein, "soft-field tomography" refers generally to any tomographic or multidimensional extension of a tomographic method that is not "hard-field tomography".

An excitation driver 26 and a response detector 28 are coupled to one or more of the transducers 24, and are each connected to a processor 30 (e.g., a computing device), which may include other components therebetween. In one embodiment, the excitation driver 26 and the response detector 28 are physically separate devices. In other embodiments, the excitation driver 26 and the response detector 28 are physically integrated as one module. It should be noted that an excitation driver 26 may be provided in connection with at least one of the transducers 24. The processor 30 sends instructions to the excitation driver 26 through a digital to analog converter (DAC) module 32 and receives data from the response detector 28 through a data-acquisition element (DAQ) module 34.

It also should be noted that different types of excitations may be used to obtain property distribution data for use in the reconstruction process of the various embodiments. For example, electrical, magnetic, optical, thermal or ultrasound excitations, among others, may be used in combination with the various embodiments. In these different embodiments, the transducers 24 may be coupled to the object 22 in different ways and not necessarily in direct contact or only at a surface of the object 22 (e.g., electrically, capacitively, galvanically, etc. coupled).

In one embodiment, the object 22 is a human body region, such as a head, a chest, or a leg, wherein, air, blood, fat, muscle, and other tissues have different electrical conductivities. An electrical impedance distribution generated by the soft field tomography system 20 shows conditions of the internal properties (e.g., material properties) of the human body region, and thus can assist in the diagnoses of diseases, for example, associated with hemorrhage, tumor, lung function, among others. In other embodiments, the soft field tomography system 20 can be used for generating a visual representation of the electrical impedance distribution in a variety of other applications, such as for determining the material properties in a mixed flow including oil and water, or soil analysis for mine exploration, among others.

In various embodiments, the transducers 24 are formed from any suitable material used to establish an excitation (e.g., EIS compatible electrical current). For example, the transducers 24 may be formed from one or more metals such as copper, gold, platinum, steel, silver, and alloys thereof. Other exemplary materials for forming the transducers 24 include non-metals that are electrically conductive, such as a silicon based materials used in combination with micro-circuits. In one embodiment, where the object 22 is a human body region, the transducers 24 are formed from silver-chloride. Additionally, the transducers 24 may be formed in different shapes and/or sizes, for example, as rod-shaped, flat plate-shaped, or needle-shaped structures. It should be noted that in some embodiments, the transducers 24 are insulated from one another. In other embodiments, the transducers 24 can be positioned in direct ohmic contact with the object 22 or capacitively coupled to the object 22.

In operation, the transducers 24 may be used to deliver continuous or modulated electrical current such that excitation patterns may be applied across a temporal frequency range (e.g., 1 kHz to 1 MHz) at a surface of the object 22 to generate a field, such as an electromagnetic (EM) field within the object 22. The resulting surface potentials, namely the voltages on the transducers 24 are measured to determine an electrical conductivity or permittivity distribution using any suitable EIS or EIT reconstruction and/or analyzing method. For example, a visual distribution may be reconstructed based on one or more of the geometry of the transducers 24, predicted voltages, the applied currents and the measured voltages.

Thus, in various embodiments, the excitation driver 26 applies an excitation to each of the transducers 24. It should be noted that any type of excitation may be provided, for example, electrical current, electrical voltage, a magnetic field, a radio-frequency wave, a thermal field, an optical signal, a mechanical deformation and an ultrasound signal, among others. In an example embodiment, the excitation driver 26 applies a direct current or an alternating current to each of the transducers 24. The excitation driver 26 applies the currents to the transducers based on an excitation pattern stored in a processor 30. The processor 30 includes an transducer fault module 31 that generates the excitation patterns during determined transducer fault conditions. In the illustrated embodiment for obtaining measurements of a human body region, the electrical current applied to the transducers 24 is sufficient to generate a measurable response of the human body region to the applied current. In another embodiment, the excitation driver 26 may include at least one voltage source for applying a voltage to each of the transducers 24.

In some embodiments, the response detector 28 measures a response $V_m$, on each of the transducers 24 (which may be multiplexed by a multiplexer) in response to the excitation applied on the transducers 24, and a resulting EM field or EM field change within the object 22. In one embodiment, the response detector 28 includes a voltage measurement module or a current measurement module to measure a response voltage or a response current on the transducers 24 in response to the current or voltage applied by the excitation driver 26. The response detector 28 also may include a multichannel analog-signal-conditioning-circuit (not shown) that amplifies and/or filters the measured response voltage or current. In other embodiments, the processor 30 includes a signal conditioning circuit for amplifying and/or filtering the response voltage or response current received from the response detector 28.

The response detector 28 can communicate the measured data to the processor 30 in real-time. Thus, in some embodiments, the response detector 28 sends the response voltage or current through the DAQ 34 to the processor 30 without perceptible delay, except for the time period for processing the data. In other embodiments, the response detector 28 communicates with the processor 30 at determined time intervals to communicate the acquire data.

It should be noted that any suitable soft field tomography method for generating a distribution of properties of the internal structure of the object 22 may be used, such as with the processor 30 defining a geometry of the object 22, and discretizing the geometry into a structure having a plurality of nodes and elements. Thus, in the example illustrated in FIG. 2, the excitation driver 26 applies an excitation pattern on the geometry by applying a load current 40 on each of the transducers 24. The response detector 28 is illustrated as having a plurality of voltage measuring devices, such as voltmeters 42, for measuring a voltage at the surface of the object 22 at the transducers 24. It should be noted that the excitation pattern and measured response are simplified for illustration and the excitation and conductivity distribution may be more complex. Additionally, the illustrated values are again provided for simplicity and ease of understanding.

Figure 3:
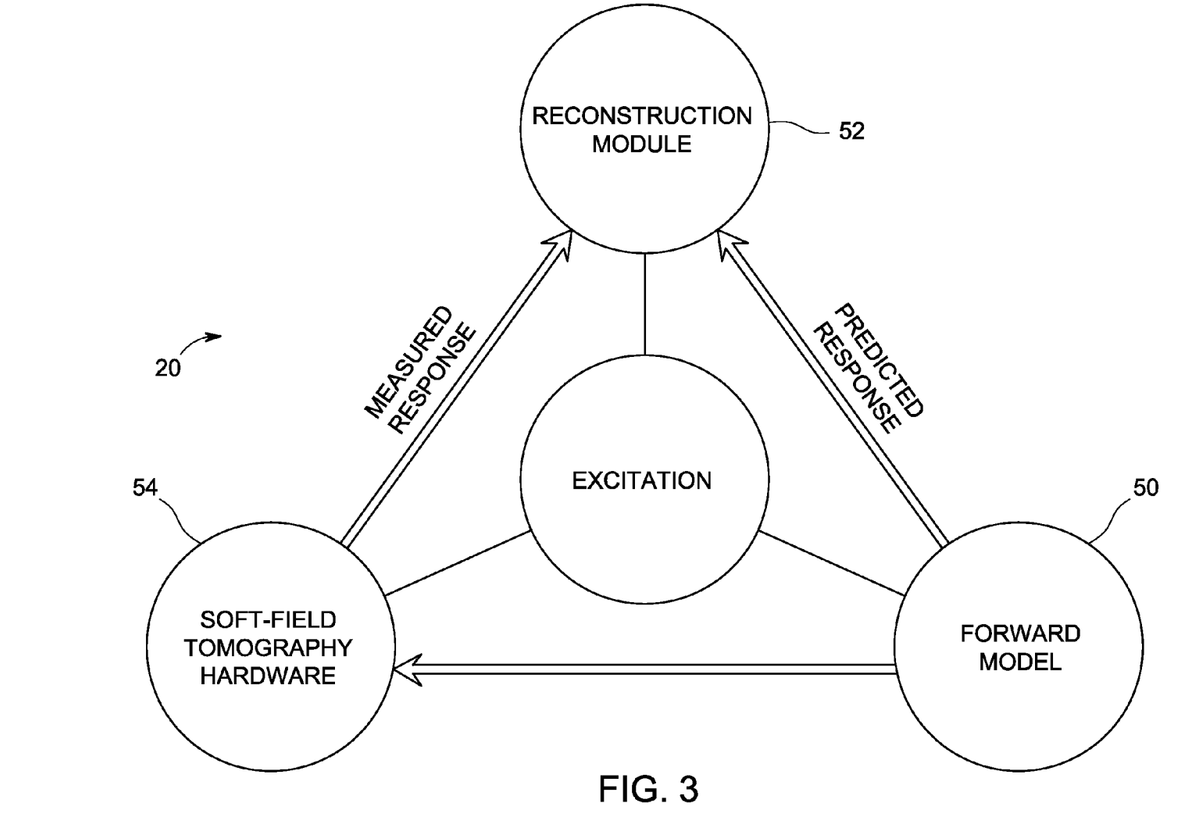
FIG. 3 is a simplified diagram illustrating data flow within a soft-field tomography system formed in accordance with various embodiments.

The processor 30, thus, computes a response of the geometry to the applied excitation. For example, as illustrated in FIG. 3, the soft field tomography system 20 uses a forward model 50 based on default excitations to predict responses (predicted response) that are provided to a reconstruction module 52. The default excitations are applied to the object 22 (shown in FIGS. 1 and 2) via soft field tomography hardware 54, which include the transducers 24 and other measurement components, with measured responses (measured response) provided also to the reconstruction module 52. Using one or more suitable soft field tomography reconstruction methods, and as described herein, a spatial distribution of the electrical properties (conductivity and/or permittivity) of the object 22 is then generated. For example, a Newton One Step Error Reconstructor (NOSER) or iterative solver (Gauss-Newton iterations approach) may be used by forward modeling the response and using an error term on the measured and predicted responses to converge to a solution.

Figure 4:
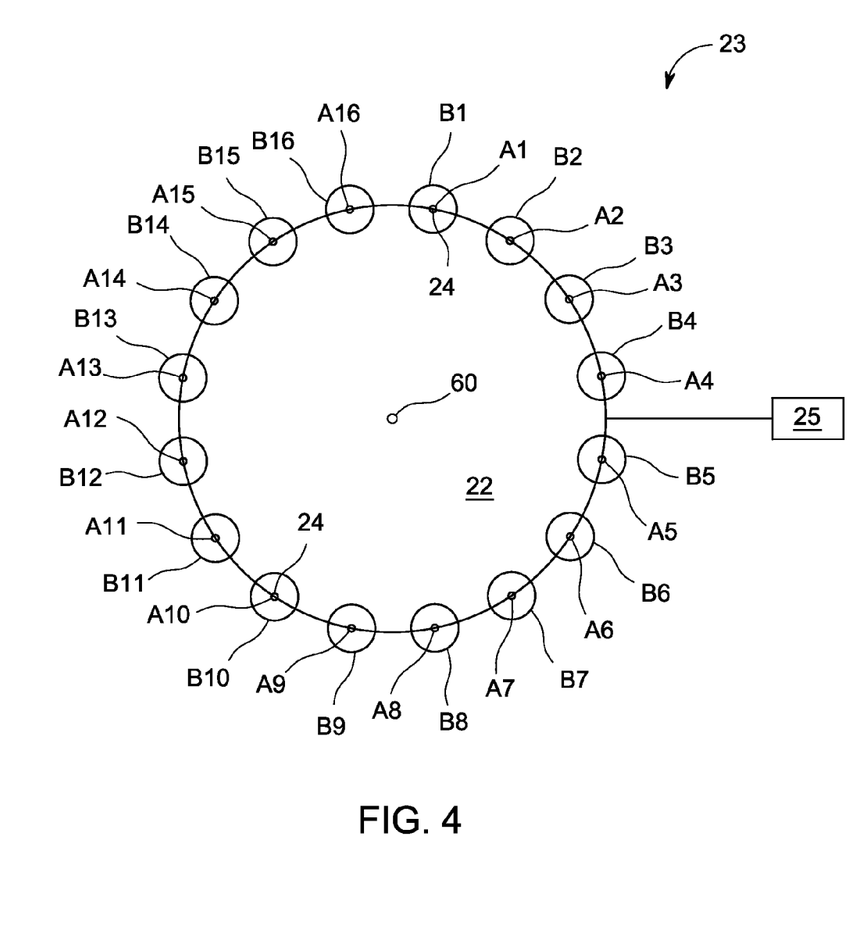
FIG. 4 illustrates an transducer configuration in accordance with various embodiments having a fault condition.

FIG. 4 is a diagram illustrating an transducer configuration 23 having a fault condition. The transducers 24 may be positioned about an axis of symmetry 60 at a surface of the object 22. In the example illustrated in FIG. 4, the transducers are positioned in a circle around the object 22. It should be noted that in various other embodiments, the dimension of symmetry 60 may be any suitable dimension of symmetry, for example, a cylinder, sphere, or the like. The transducer configuration 23 of FIG. 4 includes sixteen transducers 24 numbered $A_1$ through $A_{16}$. The transducers 24 are arranged in positions $B_1$ through $B_{16}$. In the exemplary embodiment, the transducer $A_1$ is arranged at position $B_1$ and so on. The response detector 28 measures a response at each transducer 24.

FIG. 4 illustrates a fault condition in the transducer configuration 23. In the illustrated embodiment, the fault condition exists at transducer $A_1$. In an exemplary embodiment where the transducers are surface-contacting electrodes, the fault condition may be an unacceptably high electrode-contact impedance at the electrode $A_1$ (e.g., an electrode-contact impedance above a predetermined threshold value), a disconnection of the electrode $A_1$, or other properties that render the use of the electrode to be undesirable or not possible. In one embodiment, when a fault condition exists, the sum of currents through transducers $A_1$ through $A_{16}$ does not equal to 0. Accordingly, the default excitation pattern is no longer suitable for determining electrical distribution within the object 22. In particular, the fault condition may affect the system robustness and create a loss of data prior to user intervention to correct the fault condition. It should be noted that although FIG. 4 illustrates a single fault condition at the transducer $A_1$, the fault condition may exist at any transducer 24 and/or at a multiplicity of transducers 24.

Figure 5:
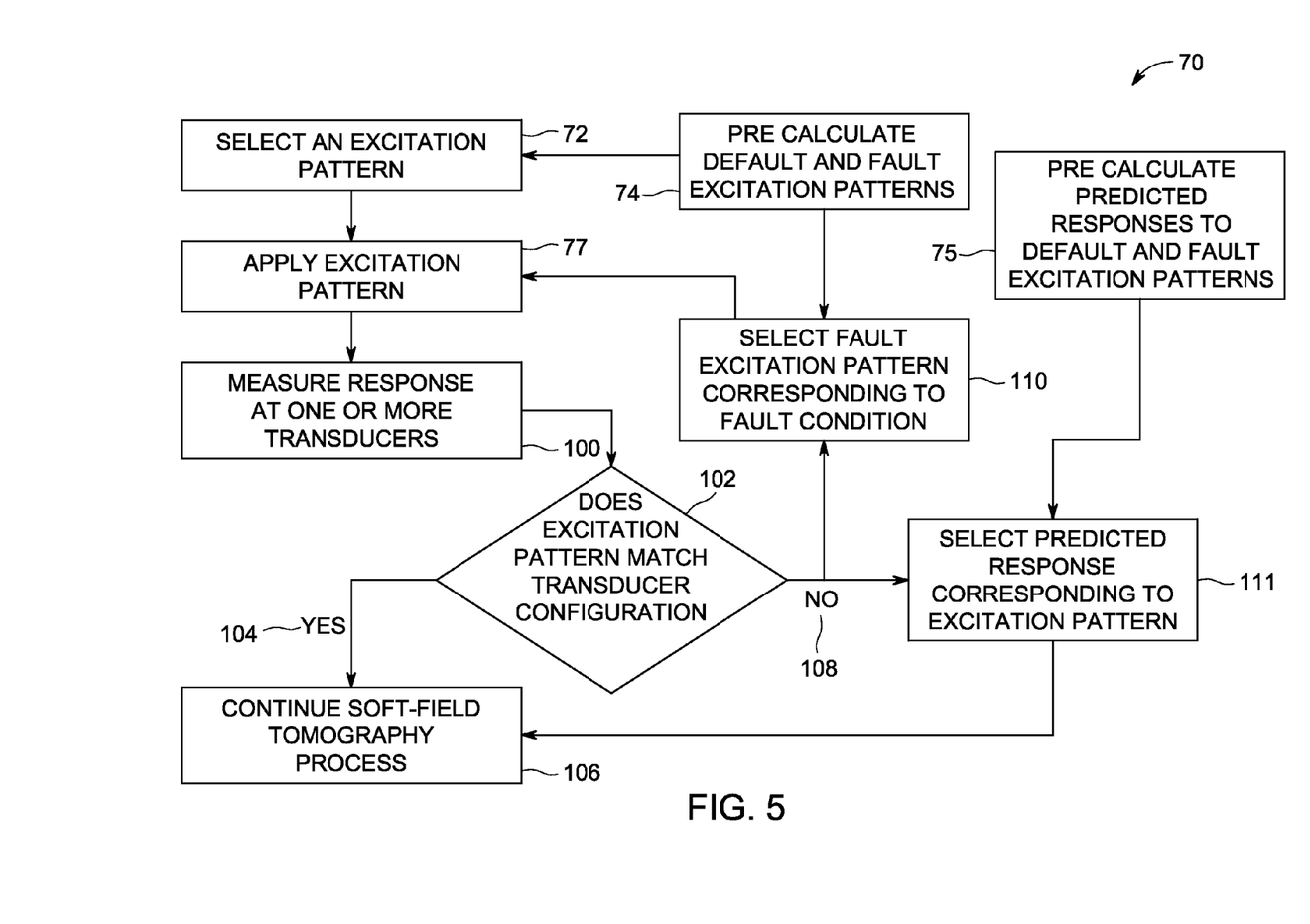
FIG. 5 illustrates a method in accordance with various embodiments for operating a soft-field tomography system during a default or a fault condition.

FIG. 5 illustrates a method 70 for operating the soft field tomography system 20 during a fault condition, for example, the fault condition illustrated in FIG. 4. At 74, one of the processor 30 or the transducer fault module 31 of the processor 30 precalculates a default excitation pattern, fault excitation patterns, and corresponding predicted responses for one or a plurality of fault conditions. In one embodiment, the default excitation pattern, fault excitation patterns, and corresponding predicted responses are apriori information. The default excitation pattern and corresponding predicted response are based on default conditions wherein a fault condition is not present. The default excitation pattern and corresponding predicted response may be computed based on assumptions which may include at least one of a number of transducers 24, a relative position of the transducers 24, and/or a geometry of a surface of the object 22. It should be noted that these default excitation patterns and corresponding predicted responses may be predetermined settings (e.g., factory settings) stored within the soft field tomography system 20.

The fault excitation patterns are calculated for fault conditions including but not limited to an unacceptably high transducer contact impedance and/or a disconnection of one or more transducers 24. For example, referring back to FIG. 4, a fault excitation pattern may be precalculated for a fault condition, wherein an unacceptably high transducer contact impedance and/or a disconnection is experienced at transducer $A_1$. The processor 30 precalculates one or a plurality of fault excitation patterns for one or a multiplicity of conditions and stores the fault excitation patterns. At 75, the transducer fault module 31 precalculates a predicted response for the default excitation pattern, for each fault excitation pattern, and for each corresponding transducer configuration.

Figure 6:
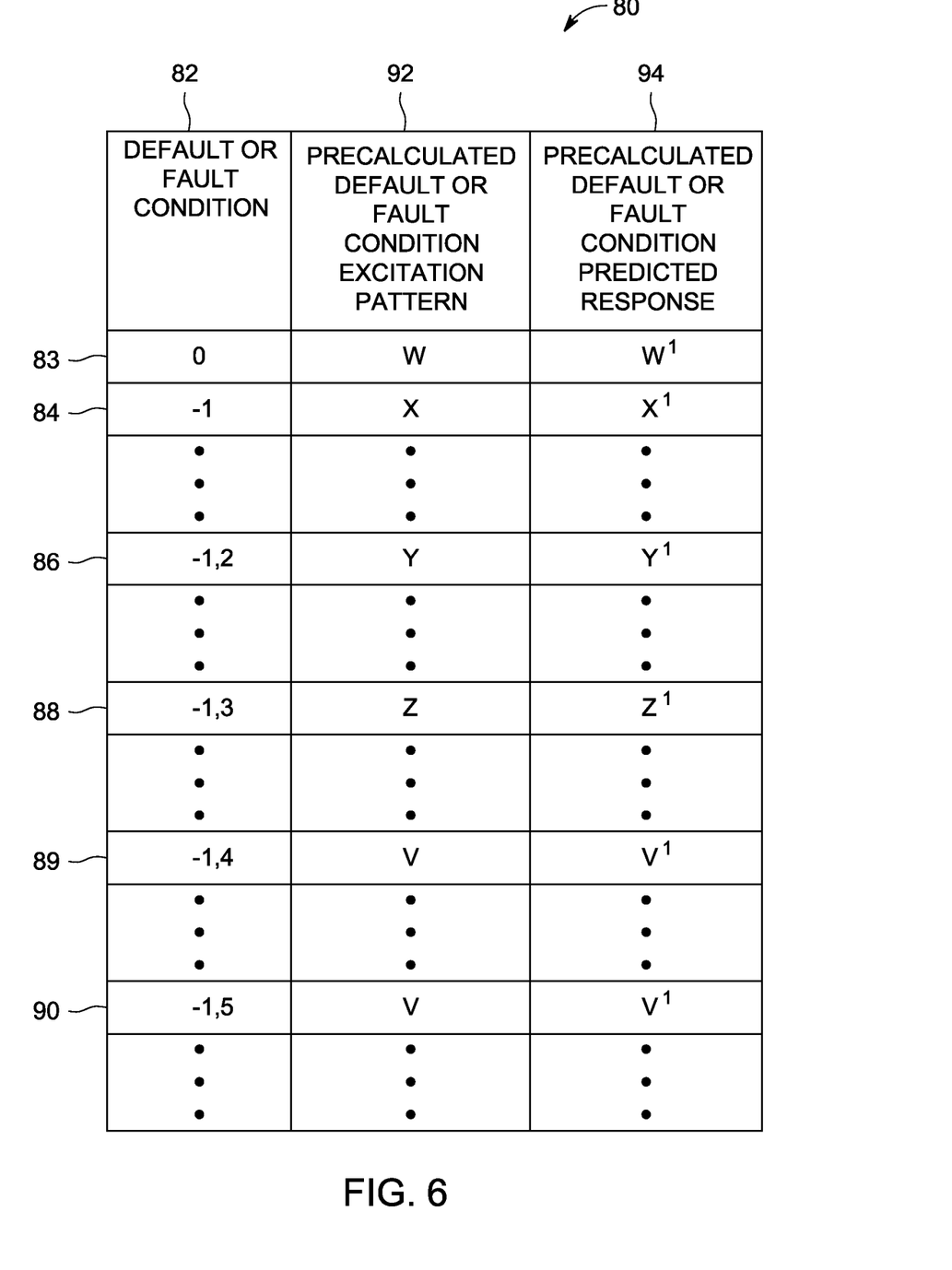
FIG. 6 illustrates a chart showing a plurality of fault conditions and corresponding fault excitation patterns and predicted responses.

FIG. 6 illustrates a chart 80 that represents a plurality of excitation patterns and corresponding predicted response for corresponding default or fault conditions. Column 82 illustrates a fault condition for a transducer configuration. For example, the default condition may exist at 83 for a default transducer configuration W and corresponding default predicted response W', the fault condition may exist at 84 for a fault condition at the transducer $A_1$, at 86 for a fault condition at transducers $A_1$ and $A_2$, at 88 for a fault condition at transducers $A_1$ and $A_3$, at 89 for a fault condition at transducers $A_1$ and $A_4$, or at 90 for a fault condition at transducers $A_1$ and $A_5$. It should be noted that the fault conditions 84, 86, 88, 89, and 90 are exemplary only, and in various embodiments, fault excitation patterns and corresponding predicted responses may be precomputed for fault conditions involving any and/or all transducers or combinations thereof. Column 92 illustrates the excitation pattern that is precalculated for each default or fault condition and column 94 illustrates the predicted response for the default or fault excitation pattern illustrated in column 92. For example, if the fault condition 84 exists, the fault excitation pattern X will be utilized to correct the fault condition. In the illustrated embodiment, the fault excitation pattern X has the predicted response of $X^1$. The fault excitation patterns and corresponding predicted responses are stored in the processor for use when a fault condition exists.

Referring back to FIG. 5, at 72, one or more of the processor 30 or the transducer fault module 31 of the processor 30 selects an excitation pattern. At 77, the processor may initially apply an excitation pattern. For example, the processor 30 may initially apply a default excitation pattern. At 100, the response detector 28 measures a response at one or more of the transducers 24. For example, the response detector 28 may measure an amplitude, phase, frequency, and/or voltage of one or more of the transducers 24. At 102, the processor 30 determines whether the excitation pattern that has been applied matches the configuration of the transducers. For example, the response at the plurality of transducers 24 may include an amplitude, a phase, a frequency, or a voltage matching or exceeding a predetermined value. If the soft field tomography system is operating without a fault condition (i.e., a fault condition does not exist) 104, at 106, the soft field tomography system is continued using a corresponding predicted response selected at 111. For example, the default excitations may continue to be used and the corresponding predicted response is selected, at 111, so that a property distribution is determined based in part on the precalculated default excitation pattern and the precalculated predicted response that were calculated at 74 and 75.

If a fault condition is detected, the processor 30 determines that a fault condition does exist, at 108. If a fault condition exists, the processor 30 selects, at 110, a fault excitation pattern that corresponds to the fault condition. The fault excitation pattern is then applied at 77. In one embodiment, the processor 30 may select at 111, a predicted response that corresponds to the fault excitation pattern selected at 110. For example, the processor 30 may select the fault excitation pattern and predicted response based on the fault excitation patterns and predicted responses stored in the chart illustrated in FIG. 6. The processor 30 selects the fault excitation pattern to approximate or match the configuration of transducers with fault conditions. At 106, the processor 30 uses the corresponding fault excitation pattern and corresponding predicted response to continue the soft-field tomography process. In the illustrated embodiment, the soft field tomography system 20 selects the fault excitation pattern and corresponding predicted response in real time during the soft-field tomography process. Accordingly, the soft field tomography system 20 does not have to be shut down and/or the soft-field tomography process does not have to be interrupted to correct a fault condition. Accordingly, the soft field tomography system operates under fault conditions. For example, the fault excitation pattern is used and the corresponding predicted response are used such that an electrical distribution is determined based in part on the precalculated fault excitation and the corresponding precomputed predicted response.

The detection of a transducer failure, at 102, may also be accomplished in other embodiments by independent transducer tests, such as tests similar to tests used in electrocardiography (ECG) for leads-off detection and electroencephalography (EEG) for electrode impedance measurement. If a fault condition is corrected during operation, the processor 30 may select a new fault excitation pattern and predicted response corresponding to the remaining fault conditions. If all fault conditions are corrected during operation, the processor may revert back to the precomputed default excitation pattern and corresponding predicted response for the default transducer configuration. The processor may dynamically select new excitation patterns and predicted responses in real time so that the soft field tomography system 20 does not have to be shut down or the soft-field tomography process does not have to be interrupted to correct fault conditions and/or changes in the fault conditions.

Figure 7:
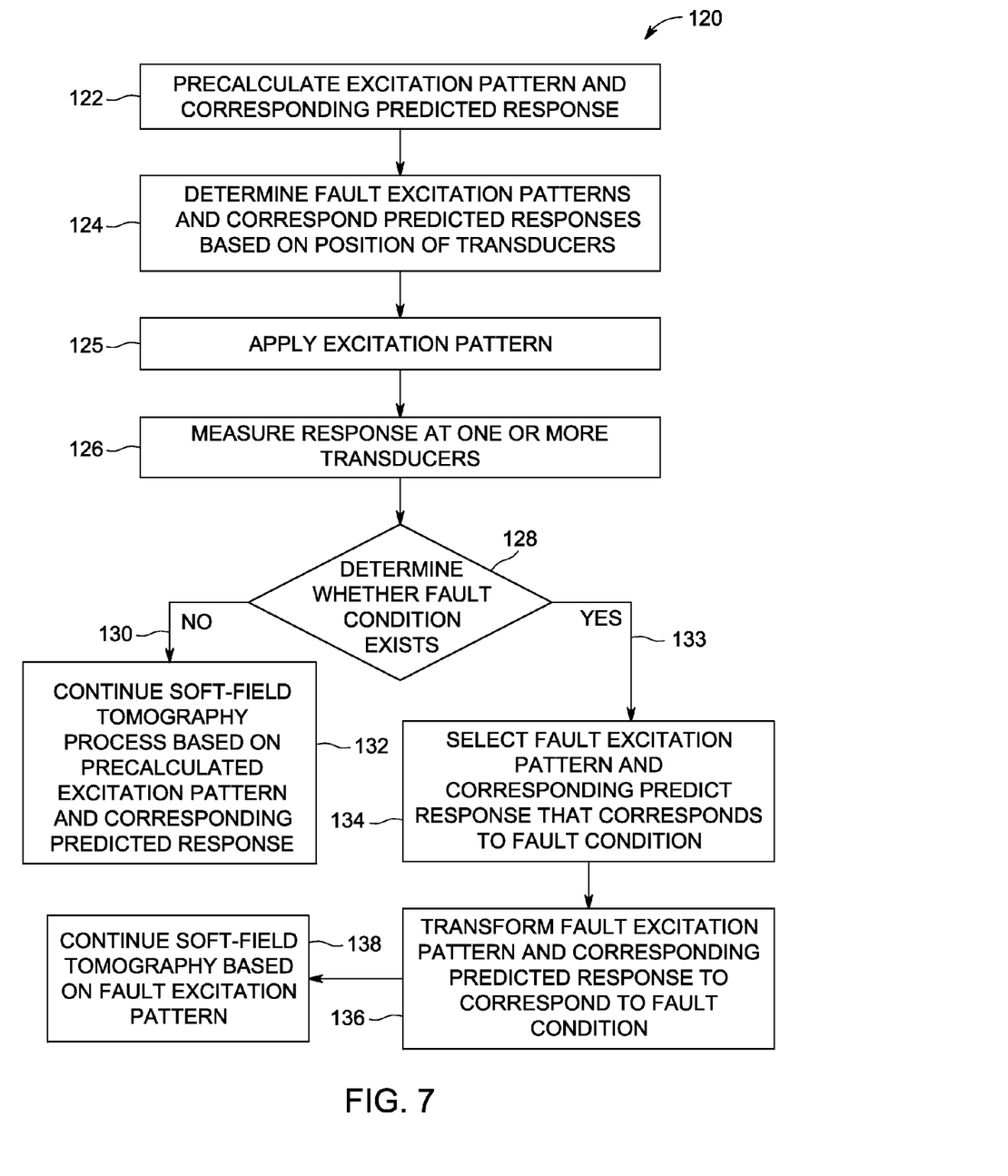
FIG. 7 illustrates a method in accordance with another embodiment for operating a soft-field tomography system during a default or a fault condition.

FIG. 7 illustrates a method 120 in accordance with another embodiment for operating the soft field tomography system 20 during a fault condition. In this embodiment a reduced number of fault detection excitation patterns are precalculated and thereafter adjusted (e.g., transformed), such as in real time, based on the location of the transducer fault. At 122, the processor 30 precalculates the excitation pattern and corresponding predicted response for the transducer configuration. The excitation pattern may be based on default conditions wherein a fault condition is not present. The excitation pattern may be computed based on at least one of a number of transducers 24, a relative position of the transducers 24, and/or a geometry of a surface of the object 22. The excitation pattern may be calculated in part based on a sum of currents through transducers $A_1$ through $A_{16}$ being 0. At 122, the processor 30 precalculates a reduced number of fault excitation patterns and corresponding predicted responses for a plurality of fault conditions that correspond to one or more mathematical transforms of the transducer positions. The mathematical transformations may include coordinate transformations, linear transformations, non-linear transformations, geometric transformations, and/or any other suitable transformation. The fault excitation patterns are calculated for fault conditions such as an unacceptably high transducer contact impedance and/or a decoupling of one or more transducers 24 from either the object and/or the hardware. In this embodiment, the fault excitation patterns and corresponding predicted responses are calculated for different combinations of transducer faults, but not for every position. For example, in the condition where there is a single transducer fault, the fault excitation pattern and corresponding predicted response is precalculated for one transducer and then used to generate a fault excitation pattern and corresponding predicted response for any single transducer fault condition that is a mathematically transformed equivalent to the position of that transducer. The processor 30 precalculates fault excitation patterns and corresponding predicted responses for multiple transforms and stores the fault excitation patterns, which are a reduced set of fault excitation patterns and corresponding predicted responses as described in more detail herein. For example, the processor 30 may calculate fault excitation patterns and corresponding predicted responses for a fault condition where a single transducer 24 is disconnected, where adjacent transducers 24 are disconnected, and/or where transducers 24 that are positioned across from one another are disconnected. The processor 30 does not calculate excitation patterns and corresponding predicted responses for each possible fault condition, but rather, generates a reduced set of fault excitation patterns and corresponding predicted responses based on a mathematical transform of the transducer positions.

At 125, the precalculated excitation pattern is applied. At 126, the response detector 28 measures a response of one or more of the transducers 24. For example, the response detector 28 may measure an amplitude, phase, frequency, and/or voltage of one or more of the transducer 24. At 128, the processor 30 determines whether a fault condition exists based on the measured response of at least one transducer 24. In a scenario where a fault condition does not exist 130, the soft field tomography system 20, at 132, executes the soft-field tomography process based on at least one of the precalculated excitation pattern and corresponding predicted response that were precalculated at 122. If a fault condition exists 133, the processor 30 selects, at 134, a fault excitation pattern and corresponding predicted response that corresponds to mathematical transform of the location of the fault condition. For example, in the case of electrodes in a configuration having rotational symmetry, if the fault condition includes a single disconnected transducer, a fault excitation pattern for a single transducer 24 is selected and the excitation pattern and corresponding predicted response are transformed (e.g., rotated, stretched, twisted, folded, or the like) to align the precomputed fault excitation pattern and corresponding predicted response to the transducer exhibiting the fault. In one embodiment, the transformation may include a uniform or non-linear expansion of the excitation pattern or predicted response.

In another example, if the fault condition includes adjacent transducers 24 that have become disconnected, a fault excitation pattern and corresponding predicted response for adjacent transducers is selected. The excitation pattern and corresponding predicted response are transformed to align the precomputed fault excitation pattern and corresponding predicted response to the adjacent transducers exhibiting the faults. The fault excitation pattern and corresponding predicted response are selected based on the one or more fault locations and one or more transforms of the excitation pattern and corresponding predicted response to the fault condition locations. For example, in a two-dimensional geometry with rotational symmetry, if a single fault exists at a transducer in position $B_3$, a fault excitation pattern and corresponding predicted response is selected for a single fault at any position. At 136, the fault excitation pattern and corresponding predicted response are transformed so that the fault excitation pattern and corresponding predicted response match the location of the fault condition. For example, the fault excitation and corresponding predicted response corresponding to a single fault is transformed so that the single fault represented in the fault excitation and corresponding predicted response is positioned at the location of the transducer exhibiting the fault condition. At 138, the soft field tomography system 20 executes the soft-field tomography process based on the transformed fault excitation pattern and corresponding predicted response. By transforming the fault excitation pattern and corresponding predicted response, the transducer fault module 31 need only produce a reduced set of fault excitation patterns and corresponding predicted responses.

Figure 8:
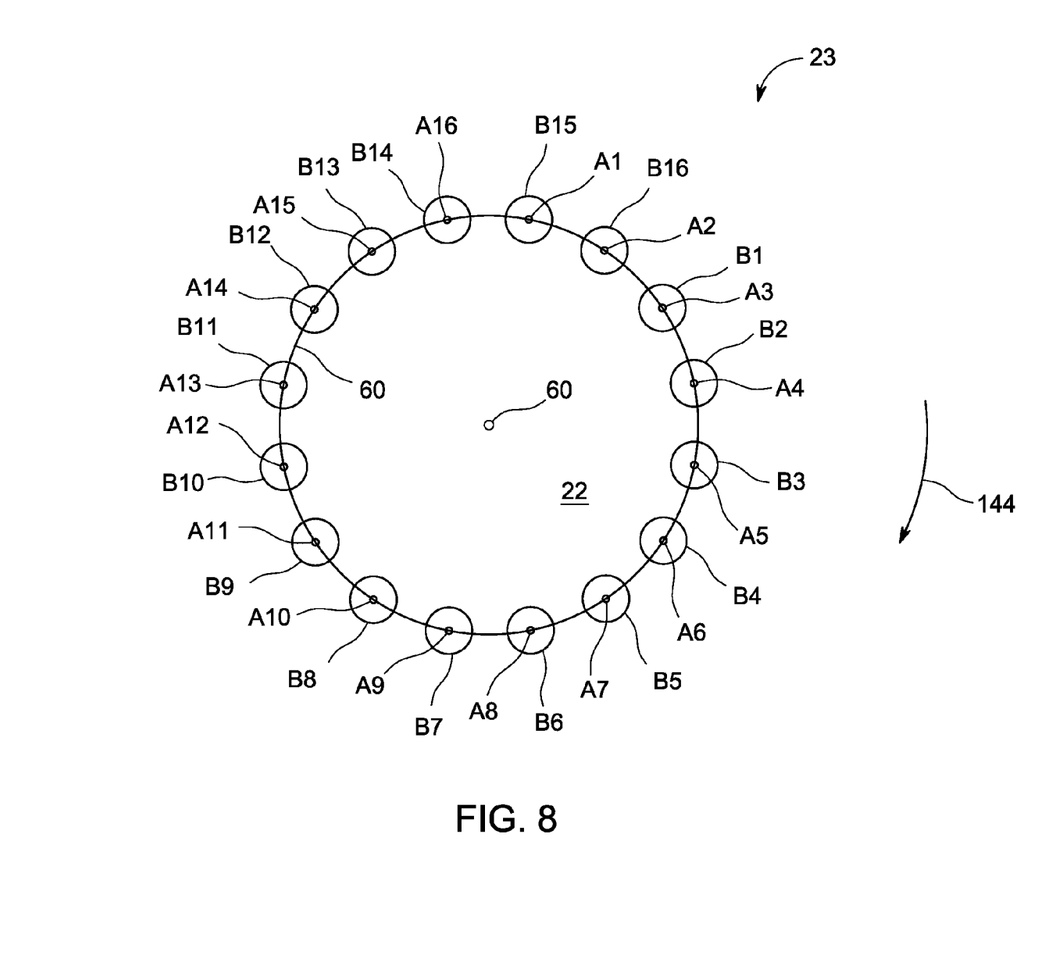
FIG. 8 illustrates an transducer configuration in accordance with another embodiment having a fault condition.

FIG. 8 illustrates the transducer configuration 23 having a fault condition. In an exemplary embodiment, the transducer configuration 23 includes the transducers $A_1$ through $A_{16}$ positioned about at least one axis of symmetry 60. In the illustrated embodiment, a fault condition exists at transducers $A_3$ and $A_4$. A fault excitation pattern and corresponding predicted response is selected for a fault condition including faults at adjacent transducers. In the illustrated embodiment, the fault excitation pattern and corresponding predicted response corresponds to faults at transducers $A_1$ and $A_2$ at positions $B_1$ and $B_2$. The fault excitation pattern and corresponding predicted response are transformed about arrow 144 so that the positions $B_1$ and $B_2$ are rotated to transducers $A_3$ and $A_4$. By transforming the fault excitation pattern and corresponding predicted response, the processor 30 is only required to store fault excitation patterns and corresponding predicted responses for a select number of symmetrical configurations. Because of the symmetry of the system, the same fault excitation pattern and corresponding predicted response for a particular transducer configuration fault condition can be used at different positions depending on the location of the transducer and one or more axes of symmetry. It should be appreciated that while rotation is used in non-limiting examples herein, there are other mathematical transforms, including geometric, linear, and non-linear transforms that may be applied to the excitation patterns and corresponding predicted responses.

In various embodiments, excitation patterns (default excitations) and corresponding predicted responses are precomputed for a given transducer configuration at a surface of an object to be interrogated using the soft field tomography system. The excitation patterns and corresponding predicted responses are based on assumptions, including, but not limited to, the number of transducers, relative transducer position, and geometry of one or more boundary or surface of the object. Additional excitation patterns (fault excitations) and corresponding predicted responses are precomputed for various single or multiple-fault conditions such as unacceptable high transducer contact impedance at one or more transducers, leads-off conditions, or a slipped transducer. When one or more of the fault conditions is detected, the fault excitation pattern and corresponding predicted response that best matches the fault condition is selected. If one of the fault conditions resolves itself, then the fault excitation pattern and corresponding predicted response that corresponds to the remaining fault conditions is applied. In this way, the soft field tomography process is always using the excitation pattern and the corresponding predicted response that is most representative of the actual transducer configuration. Accordingly, signal to noise ratios are increased or maximized and artifacts and noise in the reconstructed dataset are reduced, and data corruption is reduced or eliminated.

Although the various embodiments are described in connection with electrical excitation and electrical response, other sources of excitation and response may be provided. For example, magnetic, optical, thermal or ultrasound excitations and responses, among others, may be used in combination with the various embodiments.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as an optical disk drive, solid state disk drive (e.g., flash RAM), and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), field-programmable gate arrays (FPGAs), graphical processing units (GPUs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program, which may form part of a tangible non-transitory computer readable medium or media. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claim.

What is claimed is:

1. A soft-field tomography system comprising:
a plurality of transducers configured for positioning at a surface of an object, wherein the plurality of transducers correspond to a plurality of channels;
an excitation driver coupled to the plurality of channels and configured to generate a precomputed default excitation pattern for the plurality of transducers;
a processor electrically coupled to the excitation driver, the processor storing the precomputed default excitation pattern and a corresponding predicted response for the precomputed default excitation pattern, the processor further storing at least one precomputed fault excitation pattern and corresponding predicted response for the precomputed fault excitation pattern corresponding to one or more fault conditions of the plurality of transducers; and
a response measurement device configured to measure a response at one or more of the transducers to determine if a fault condition exists, wherein, if a fault condition exists, the processor performs at least one of instructs the excitation driver to generate at least one of the precomputed fault excitation pattern or uses the predicted response that corresponds to one or more fault conditions for a soft field tomography process.

2. The system of claim 1, wherein the precomputed fault excitation pattern and the corresponding predicted response for the precomputed fault excitation pattern are determined based on a position of the transducers, wherein the processor transforms at least one of the precomputed fault excitation pattern and the corresponding predicted response to match the fault condition.

3. The system of claim 2, wherein the processor transforms at least one of the precomputed fault excitation patterns and the corresponding predicted response through at least one of a mathematical transformation, a coordinate transformation, a linear transformation, a non-linear transformation, or a geometric transformation.

4. The system of claim 1, wherein at least one of the precomputed default excitation pattern or the corresponding predicted response is computed based on at least one of a number of transducers, a relative position of the transducers, or a geometry of the surface of the object.

5. The system of claim 1, wherein the transducers are electrodes and the precomputed fault excitation pattern and the corresponding predicted response for the precomputed fault excitation pattern are computed for fault conditions wherein an electrode contact impedance above a predetermined threshold exists for at least one of the electrodes.

6. The system of claim 1, wherein the precomputed fault excitation pattern and the corresponding predicted response are computed for fault conditions wherein at least one of the transducers becomes disconnected from the excitation driver.

7. The system of claim 1, wherein the precomputed fault excitation pattern and the corresponding predicted response are computed for fault conditions wherein at least one of the transducers becomes decoupled from the surface of the object.

8. The system of claim 1, wherein a sum of the currents of the transducers operating in the precomputed default excitation pattern equals zero, and a sum of the currents of the transducers operating in a precomputed fault excitation pattern equals zero.

9. The system of claim 1, wherein the processor selects a precomputed fault excitation pattern during a soft-field tomography process.

10. The system of claim 1, wherein a fault condition is determined to exist based on a detection of a non-zero sum of excitations on all or a subset of the plurality of transducers.

11. The system of claim 1, wherein the response at the plurality of transducers includes at least one of an amplitude, a phase, or a frequency matching or exceeding a predetermined value.

12. A method for correcting a fault condition in a soft-field tomography system, the method comprising:
    precomputing a default excitation pattern and a corresponding predicted response for a plurality of transducers arranged at a surface of an object;
    precomputing at least one fault excitation pattern and corresponding predicted response for the fault excitation pattern that correspond to one or more fault conditions in the plurality of transducers;
    applying the default excitation pattern to the object;
    measuring a response at one or more of the plurality of transducers to determine if a fault condition exists; and
    if a fault condition exists, at least one of selecting at least one fault excitation pattern or using the corresponding predicted response that corresponds to one or more fault conditions.

13. The method of claim 12 further comprising:
    computing the fault excitation pattern and the corresponding response based on a position of the transducers; and
    transforming the fault excitation pattern and the corresponding response to match the fault condition.

14. The method of claim 13 further comprising transforming the fault excitation pattern and the corresponding predicted response through at least one of a mathematical transformation, a coordinate transformation, a linear transformation, a non-linear transformation, or a geometric transformation.

15. The method of claim 12 further comprising computing the default excitation pattern and the corresponding predicted response based on at least one of a number of transducers, a relative position of the transducers, or a geometry of the object.

16. The method of claim 12, wherein the transducers are electrodes, the method further comprising computing the fault excitation pattern and the corresponding predicted response for fault conditions wherein an electrode contact impedance above a predetermined threshold exists for at least one of the electrodes.

17. The method of claim 12 further comprising computing the fault excitation pattern and the corresponding predicted response for fault conditions wherein at least one of the transducers becomes disconnected from system hardware or decoupled from the surface of the object.

18. The method of claim 12, wherein the response at the plurality of transducers includes at least one of an amplitude, a phase, or a frequency matching or exceeding a predetermined value.

19. A processor for correcting a fault condition in a soft-field tomography system having a transducer fault module, the transducer fault module configured to:
    precompute a default excitation pattern and a corresponding predicted response for a plurality of transducers arranged at a surface of an object;
    precompute at least one fault excitation pattern and corresponding predicted response for the fault excitation pattern corresponding to one or more fault conditions in the plurality of transducers;
    apply the default excitation pattern to the object;
    measure a response at one or more of the plurality of transducers to determine if a fault condition exists; and
    if a fault condition exists, at least one of select at least one fault excitation pattern or use the corresponding predicted response that corresponds to the fault condition.

20. The processor of claim 19, wherein the transducer fault module is further configured to:
    compute the fault excitation pattern and the corresponding predicted response based on a position of the transducers; and
    transform the fault excitation pattern and the corresponding predicted response to match the fault condition.

21. The processor of claim 20, wherein the transducer fault module is further configured to transform the fault excitation pattern and the corresponding predicted response through at least one of a mathematical transformation, a coordinate transformation, a linear transformation, a non-linear transformation, or a geometric transformation.

22. The processor of claim 19, wherein the transducer fault module is further configured to compute at least one of the excitation pattern and the corresponding predicted response based on at least one of a number of transducers, a relative position of the transducers, or a geometry of the surface of the object.

23. The processor of claim 19, wherein the transducers are electrodes and the transducer fault module is further configured to compute at least one of the fault excitation pattern and the corresponding predicted response for fault conditions wherein an electrode contact impedance above a predetermined threshold exists for at least one of the electrodes.

24. The processor of claim 19, wherein the transducer fault module is further configured to compute the fault excitation pattern and the corresponding predicted response for fault conditions wherein at least one of the transducers becomes disconnected from system hardware or decoupled from the surface of the object.

25. The processor of claim 19, wherein the response at the plurality of transducers includes at least one of an amplitude, a phase, or a frequency matching or exceeding a predetermined value.

* * * * *